United States Patent

Kurono et al.

[11] Patent Number: 5,164,391
[45] Date of Patent: * Nov. 17, 1992

[54] HYDANTOIN DERIVATIVES FOR TREATING COMPLICATIONS OF DIABETES AND CIRCULATORY DISEASES

[75] Inventors: Masayasu Kurono; Ryoichi Unno; Hiromoto Kimura; Noboru Tomiya; Kiichi Sawai; Kenji Miura; Toshinao Usui; Yasuaki Kondo; Yukiya Tanaka; Shigeyoshi Nakamura; Tsunemasa Suzuki; Motohide Hayashi, all of Aichi, Japan

[73] Assignee: Sanwa Kagaku Kenkyusho Co., Ltd., Japan

[ * ] Notice: The portion of the term of this patent subsequent to Apr. 26, 2005 has been disclaimed.

[21] Appl. No.: 582,039

[22] Filed: Sep. 13, 1990

[30] Foreign Application Priority Data

Sep. 20, 1989 [JP] Japan .................................. 1-242301
Apr. 27, 1990 [JP] Japan .................................. 2-110136
Apr. 27, 1990 [JP] Japan .................................. 2-110137

[51] Int. Cl.$^5$ .............. C07D 491/107; A61K 31/495; A61K 31/415; A61K 31/445
[52] U.S. Cl. .................. 514/253; 514/232.5; 514/233.5; 514/317; 514/318; 514/320; 514/324; 514/389; 544/70; 544/230; 546/15; 548/301.1
[58] Field of Search ............... 548/309; 544/70, 230; 546/15; 514/233.5, 253, 320, 324, 389

[56] References Cited

U.S. PATENT DOCUMENTS

| | | | |
|---|---|---|---|
| 4,740,517 | 4/1988 | Kurono et al. | 546/15 |
| 4,780,472 | 10/1988 | Ueda et al. | 548/309 |
| 4,861,792 | 8/1989 | Kurono et al. | 546/15 |
| 4,978,758 | 12/1990 | Kurono et al. | 548/309 |

OTHER PUBLICATIONS

Kurono et al., Chemical Abstracts, vol. 106, No. 5042 (1987) (Abstract for EP 193415, Sep. 3, 1986).
Kinoshita et al.,, Jap. J. Ophthalmol. vol. 20: 399–410, 1976.
Gabbay, Int. Congr. Ser. Excerpta Med., 403,594 (1977).
Peterson et al., Metalbolism, vol. 28, No. 4, Suppl. 1 (Apr.), 1979.
Taguma et al., New England Journal of Medicine, vol. 313, No. 26, 1617, 1985.
Parying et al., British Medical Journal, vol. 294: 1443, 1987.

Primary Examiner—Mukund J. Shah
Assistant Examiner—E. Bernhardt
Attorney, Agent, or Firm—Nikaido, Marmelstein, Murray & Oram

[57] ABSTRACT

The invention relates to a hydantoin derivative, salt thereof, process for the preparation thereof, and medicine containing the derivative. The derivative is represented by the formula

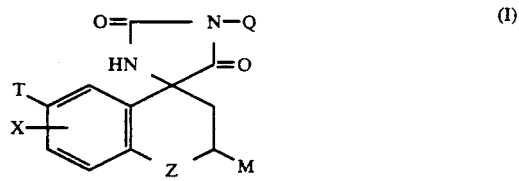

wherein M is $-CONH-NHR^1$ group, $-CONH-OR^2$ group,

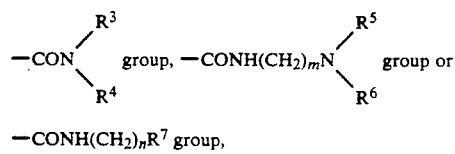

$-CONH(CH_2)_nR^7$ group, in which $R^1$ is hydrogen atom, an alkyl group, an alkenyl group, a phenyl radical, a substituted phenyl group, a naphthyl radical, a substituted naphthyl group, a pyridyl radical, a furyl radical or a thienyl radical, $R^2$ is a hydrogen atom, an alkyl group, a phenyl radical or a substituted phenyl group, $R^3$ and $R^4$ are the same or different independently, each being a phenyl radical, or an aralkyl group, or $R^3$ may form a substituted or non-substituted $C_{5-6}$ saturated heterocyclic ring together with $R^4$ and a possible nitrogen or oxygen atom, $R^5$ forms a substituted or non-substituted saturated heterocyclic ring together with $R^6$ and a possible nitrogen or oxygen atom, $R^7$ is a nitroxy radical or a heteroaryl group, $m$ and $n$ are an integer of 2 to 5, Q is a hydrogen atom or

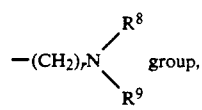

in which $R^8$ and $R^9$ are the same or different independently, each being a substituted or non-substituted alkyl group, or $R^8$ may form a substituted or non-substituted $C_{5-6}$ saturated heterocyclic ring together with $R^9$ and a possible nitrogen or oxygen atom, $r$ is an integer of 2 to 5, T and X are the same or different independently, each being a hydrogen atom, a halogen atom, an alkyl group, an alkoxy group or an alkylmercapto group, and Z is an oxygen or sulfur atom.

The derivatives and salts thereof are useful for the treatment of complications of diabetes and circulatory diseases.

2 Claims, No Drawings

HYDANTOIN DERIVATIVES FOR TREATING COMPLICATIONS OF DIABETES AND CIRCULATORY DISEASES

BACKGROUND OF THE INVENTION

1. Field of the Invention

The present invention relates to novel hydantoin derivatives, salts thereof, a process for the preparation thereof and a medicine comprising at least one of the derivatives or the salts as an effective ingredient to treat complications of diabetes and/or to prevent or cure circulatory diseases.

2. Related Arts

Hitherto, various studies have been made to find out an effective compound for curing diabetes, which compound can be formulated into a medicine for oral dosage. As a result, various drugs, each of which comprises as an effective ingredient, sulfonyl urea, mesooxalate, a guanidine derivative or the like have been developed and marketed for clinical use, but those are mere symptomatic treating agents to a hyperglycoplasmia due to the diabetes. It has been known there may be caused due to the diabetes specific chronic complications such as diabetic cataract, diabetic neuropathy, diabetic retinopathy and the like, but there is almost no effective agent for curing the complications and it may be said that no effective therapeutic system has been established.

Therefore, hitherto, various studies have also been made for developing an effective compound for curing such intractable diseases due to the diabetes but it is the fact that there has been is almost no success case. As one of studies for developing a compound for curing the complications of diabetes, there is a search on an anti- or inhibition substance to enzyme of aldose reductase, since the enzyme reduces in vivo of human being, and other animals, aldoses such as glucose and galactose into corresponding polyols such as sorbitol and galactitol and it has been known that the complications will appear when the formed sorbitol and galactitol are accumulated at crystalline lens, peripheral nerve, kidney or the like tissue or organ in patients with the diabetes or galactosemia ["Jap. J. Opthamol.", Vol. 20, page 399 (1976); Int. Congr. Ser. Excepta Med.", pages 403 and 594 (1977); and "Metabolism", Vol. 28, page 456 (1979)].

Some of the inventors and researchers in the assignee company have also studied and investigated substances showing the inhibition to aldose reductase to find out various hydantoin derivatives [Jap. Pat. Sho 61-200991(A) corresponding to U.S. Pat. No. 4,740,517 and EP 0193415(A2); and Jap. Pat. Nos. Sho 61-199924(A) and 61-126881(A) corresponding to U.S. Pat. No. 4,861,792 and EP 0264586(A1)].

Further, it has been known that there is a close relation between diabetes and circulatory diseases, since the arteriosclerosis is the complications of diabetes, which is caused with the highest frequency in occurrence and one of causes thereof lies in metabolic abnormality of lipids due to the diabetes. Moreover, a patient with a diabetic nephropathy has been often complicated with a circulatory disease of a hypertonia. In connection with this, such a report has been issued that a reduction in renal function of patients with diabetes can be delayed by carrying out a treatment for circulatory diseases and more particularly by dosing a hypotensor ["Br. Mrd. J.", Vol. 294, page 1443 (1987) and "N. Eng. J. Med.", Vol. 313, page 1617 (1985)].

SUMMARY OF THE INVENTION

A primary object of the invention is to provide novel hydantoin derivatives other than those having been developed by the parties belonging to the assignee company discussed above, each of which shows an inhibition to the enzyme of aldose reductase, thereby inhibiting an accumulation of sorbitol, galactitol and the like polyols in a living body, to affect the prevention and/or curing of intractable complications of diabetes possible.

A secondary object of the invention is to provide novel hydantoin derivatives with a low toxicity, and thus having excellent safety of use.

A tertiary but important object of the invention is to provide novel hydantoin derivatives which also shown an action to the circulatory system (depressing action of blood pressure), in addition to the inhibition to aldose reductase, so that the accumulation of polyols in a living body and occurrence of circulatory disease can be concurrently inhibited, to make concurrent curing of the complications of diabetes and circulatory diseases possible.

According to the invention, the objects can basically be attained by a hydantoin derivative of the formula

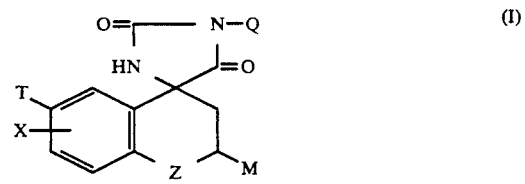

wherein M is —CONH—NHR$^1$ group, —CONH—OR$^2$ group,

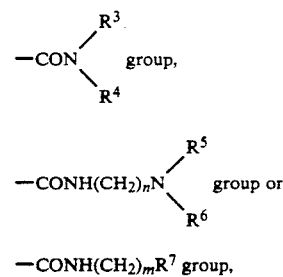

—CONH(CH$_2$)$_m$R$^7$ group, in which R$^1$ is hydrogen atom, an alkyl group, an alkenyl group, a phenyl radical, a substituted phenyl group, a naphthyl radical, a substituted naphthyl group, a pyridyl radical, a furyl radical or a thienyl radical, R$^2$ is a hydrogen atom, an alkyl group, a phenyl radical or a substituted phenyl group, R$^3$ and R$^4$ are the same or different independently, each being a hydrogen atom, an alkyl group, a phenyl radical, a substituted phenyl group or an aralkyl group, or R$^3$ may form a substituted or non-substituted C$_{5-6}$ saturated heterocyclic ring together with R$^4$ and a possible nitrogen or oxygen atom, R$^5$ forms a substituted or non-substituted saturated heterocyclic ring together with R$^6$ and a possible nitrogen or oxygen atom, R$^7$ is a nitroxy radical or a heteroaryl group, $n$ and $m$ are an integer of 2 to 5, Q is a hydrogen atom or

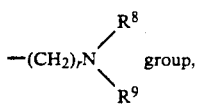

in which $R^8$ and $R^9$ are the same or different independently, each being a substituted or non-substituted alkyl group, or $R^8$ may form a substituted or non-substituted $C_{5-6}$ saturated heterocyclic ring together with $R^9$ and a possible nitrogen or oxygen atom, $r$ is an integer of 2 to 5, T and X are the same or different independently, each being a hydrogen atom, a halogen atom, an alkyl group, an alkoxy group or an alkylmercapto group, and Z is an oxygen or sulfur atom, or a pharmaceutically acceptable salt thereof.

Namely, it has been confirmed that derivatives (I) show an effective inhibition to aldose reductase, acts to the circulatory system and has a quite low toxicity.

In derivatives (I), the alkyl group may be straight-chain alkyl radicals, branched-chain alkyl radicals or cycloalkyl radicals. As examples for the straight-chain alkyl radicals, one having 1 to 10 carbon atoms, for instance methyl, ethyl, n-propyl, n-butyl, n-pentyl, n-hexyl or the like may be listed. As the branched-chain alkyl radicals, isopropyl, isobutyl, s-butyl, t-butyl and the like may be listed. As the cycloalkyl radicals, one having three or more carbon atoms, for instance cyclopropyl, cyclobutyl, cyclopentyl, cyclohexyl and the like may be listed. As the alkenyl group, for instance, allyl and the like may be listed. As the substituent for substituted phenyl or naphthyl, fluorine, chlorine, bromine and the like halogen atom, as well as methoxy, ethoxy and the like alkoxy group may be listed. The number of the substituent may be of more than one. As examples for the

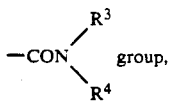

wherein the substituents $R^3$ and $R^4$ represent together a heterocyclic ring which may include a nitrogen or oxygen atom therein, pyrrolidino, morpholino, piperidino, piperazino and the like may be listed. As examples for the

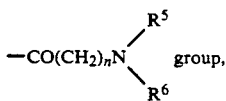

wherein the substituents $R^5$ and $R^6$ represent together a substituted or non-substituted saturated heterocyclic ring which may include a nitrogen or oxygen atom therein, pyrrolidino, piperidino, piperazino, morpholino and the like may be listed. As the heteroaryl group, imidazolyl and the like may be listed. As examples for the

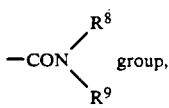

wherein the substituents $R^8$ and $R^9$ represent together a heterocyclic ring which may include a nitrogen or oxygen atom therein, pyrrolidino, morpholino, piperidino, piperazino and the like may be listed. As the halogen atom, fluorine, chlorine and iodine may be listed, but fluorine is preferable. As examples for the alkoxy group, those having a straight-chain alkyl radical, for instance methoxy, ethoxy, n-propoxy, n-butoxy, n-pentyloxy, n-hexyloxy and the like, as well as those having a branched-chain alkyl radical, for instance isopropoxy, isobutoxy, s-butoxy, t-butoxy and the like may be listed. As examples for the alkylmercapto group, those having a straight-chain alkyl radical, for instance, methylmercapto, ethylmercapto, n-propylmercapto, n-butylmercapto, n-pentylmercapto, n-hexylmercapto and the like, as well as those having a branched-chain alkyl radical, for instance isopropylmercapto, isobutylmercapto, s-butylmercapto, t-butylmercapto and the like may be listed.

In the specification, the salt of derivatives (I) means those acceptable for employing the same as an effective ingredient for a medicine. As specific examples, those with an inorganic acid such as phosphoric acid, hydrochloric acid, sulfuric acid, hydrobromic acid, hydroiodic acid or the like, an organic acid such as acetic acid, succinic acid, fumaric acid, lactic acid, tartaric acid, citric acid, methanesulfonic acid or the like may be listed.

Each of derivatives (I) according to the invention has two asymmetric carbon atoms in its structure and thus has two kinds of stereo isomers and optical isomers thereof. It should be noted that those are, of course, included in scope of the invention.

The hydantoin derivatives (I) can be prepared as stated below.

Among the derivatives, the compound of the formula

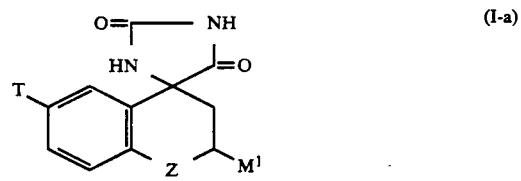

wherein T and Z have the meanings as referred to, and $M^1$ is —CONH—NHR$^1$ group or —CONH—OR$^2$ group, in which $R^1$ and $R^2$ have the meanings as referred to, can be prepared by reacting a compound of the formula

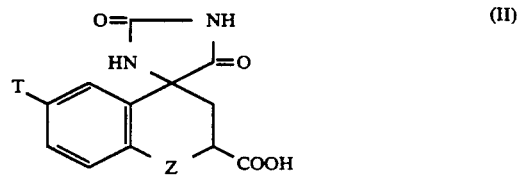

wherein T and Z have the meanings as referred to, with a halogenizing or esterifying reagent, and reacting the resulting compound of the formula $$\text{(III)}$$

[Structure III: benzene ring with T substituent, fused to a ring system containing O=C-NH, HN, =O, Z, and CO-A groups]

wherein T and Z have the meanings as referred to and A is chlorine atom, methoxy radical or n-propoxy radical, with a compound of the formula $$R^1-NHNH_2 \qquad \text{(IV)}$$

or $$R^2-ONH_2 \qquad \text{(V)}$$

wherein $R^1$ and $R^2$ have the meanings as referred to.

The compounds II and III may be prepared according to the process as disclosed in Jap. Pat. Nos. Sho 63-57588(A) and 63-250373(A).

Among the derivatives, the compound of the formula $$\text{(I-b)}$$

[Structure I-b with T, X, Z, and $M^2$ substituents]

wherein T, X and Z have the meanings as referred to, and $M^2$ is $$-CONH(CH_2)_mN\begin{matrix}R^5\\R^6\end{matrix} \text{ group or}$$

$$-CONH(CH_2)_nR^7 \text{ group,}$$

in which $R^5$, $R^6$, $R^7$, $m$ and $n$ have the meanings as referred to, can be prepared by reacting a compound of the formula $$\text{(VI)}$$

[Structure VI with T, X, Z and M' substituents]

wherein T, X and Z have the meanings as referred to, and M' is an active carbonyl radical, with a compound of the formula $$H_2N(CH_2)_mN\begin{matrix}R^5\\R^6\end{matrix}$$

wherein $R^5$, $R^6$ and $m$ have the meanings as referred to, or a compound of the formula $$H_2N(CH_2)_nR^7$$

wherein $R^7$ and $n$ have the meanings as referred to.

The starting compound (VI) may be prepared according to the process as disclosed in Jap. Pat. No. Sho 63-57588(A). The reaction can be carried out by stirring the reactants under room temperature to reflux temperature, in the presence of an inert solvent. As the inert solvent, dimethylformamide, dimethylsulfoxide dimethylacetamide, dioxane, tetrahydrofuran and the like can be listed.

Among the derivatives (I), the compound of the formula $$\text{(I-c)}$$

[Structure I-c with T, X, Z, and $M^3$ substituents, and N-Q' group]

wherein T, X and Z have the meanings as referred to, and $M^3$ is $$-CON\begin{matrix}R^3\\R^4\end{matrix} \text{ group,}$$

and Q' is $$-(CH_2)_rN\begin{matrix}R^8\\R^9\end{matrix} \text{ group,}$$

in which $R^3$, $R^4$, $R^8$, $R^9$ and $r$ have the meanings as referred to, can be prepared by reacting the compound of the formula $$\text{(VII)}$$

[Structure VII with T, X, Z and $M^3$ substituents]

wherein $M^3$, T, X and Z have the meanings as referred to, with a compound of the formula $$Hal(CH_2)_rNR^8R^9$$

wherein $R^8$, $R^9$, and $r$ have the meanings as referred to, and Hal is a halogen atom, or reacting compound (VII) with a compound $$Hal-(CH_2)_r-Hal$$

wherein Hal and $r$ have the meanings as referred to, and then the resulting compound of the formula

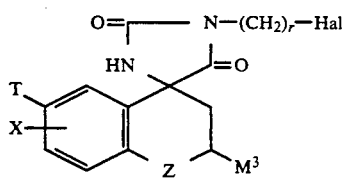

(VIII)

wherein $M^3$, T, X, Z and Hal have the meanings as referred to, with a compound of the formula $HNR^8R^9$ wherein $R^8$ and $R^9$ have the meanings as referred to.

The reaction can be carried out by reacting compound (VII) with a base, e.g. sodium hydride, potassium hydride or the like, at temperature of ice-cooling to room temperature and in the presence of a solvent, and adding the other reactant to cause the reaction at temperature of room temperature to reflux temperature. As the solvent, dimethylformamide, dimethylsulfoxide, dimethylacetamide, dioxane, tetrahydrofuran or the like may be used.

There is no specific limitation, when the derivative or salt according to the invention will be made into a medicine containing at least one of the compounds or salts, as effective ingredient. Therefore, the medicine may be of a solid form such as tablet, pill, capsule, powder, granule and suppository, or a liquid form of solution, suspension or emulsion, together with a conventional additive(s) and/or a carrier(s). The medicine of such a form can be prepared in a conventional manner. For preparing the medicine in a solid form, starch, lactose, glucose, calcium phosphate, magnesium stearate, gum arabic or the like vehicle may be used, and if necessary a lublicant, binder, disintegrating agent, coloring agent, flavour and the like may be added. For preparing the medicine of liquid form, a stabilizer, an assistance for dissolving, suspendizer, emulsifier, buffer, reserving agent or the like may be used.

A dosing amount of the derivative or salt for human being depends on the selected compound or salt per se, the condition of illness, the age of the patient, the form of the medicine and other factors, but in case of an adult, 0.1 to 3000 mg/day and more particularly 1 to 300 mg/day are preferable.

DETAILED DESCRIPTION OF PREFERRED EMBODIMENTS

The invention will now be further explained in more detail with reference to Manufacturing Examples, Pharmacological Test Examples as well as Prescription Examples.

EXAMPLE 1

(2S,4S)-6-Fluoro-2',5'-dioxospiro[chroman-4,4'-imidazolidine]-2-carbohydrazide

To a solution of (2S,4S)-6-fluoro-2',5'-dioxospiro[chroman-4,4'-imidazolidine]-2-carboxylic acid n-propyl ester (30.0 g, 93.1 mmol) in 600 ml of ethanol was added hydrazine hydrate (46.6 g, 0.931 mol). After refluxing the mixture under an argon atmosphere for 2 hours, the reaction mixture was evaporated in vacuo to dryness. To the residue was added 100 ml of saturated aqueous sodium chloride and the aqueous layer was extracted with ethyl acetate (300 ml×5). The combined ethyl acetate layers were washed with water, dried over anhydrous sodium sulfate, filtered and evaporated in vacuo to give 17.3 g (Yield: 63.1%) of crude crystals. The crystals were recrystallized from ethanol to give colorless needles of the desired compound (12.8 g, 46.7%).

Melting point: 277°-278° C.
$[\alpha]_D^{25}$: +139° (c=1.0, methanol).
IR spectrum ($v_{max}^{KBr}$) cm$^{-1}$: 3450, 3330, 3060, 1775, 1725, 1660.
NMR spectrum (DMSO-d$_6$) δ ppm:

| | |
|---|---|
| 2.13 | (1H, dd, J=14.2 and 12.4Hz), |
| 2.40 | (1H, dd, J=14.2 and 2.4Hz), |
| 4.39 | (2H, s), |
| 5.10 | (1H, dd, J=12.4 and 2.4Hz), |
| 6.9-7.2 | (3H, m), |
| 8.38 | (1H, s), |
| 9.59 | (1H, s), |
| 11.00 | (1H, s). |

Mass spectrum (EI/DI) m/z: 294 (M+, base peak), 235, 192.

EXAMPLE 2

(2S,4S)-6-Fluoro-2',5'-dioxospiro[chroman-4,4'-imidazolidine]-2-(N'-methyl)carbohydrazide To a solution of (2S,4S)-6-fluoro-2',5'-dioxospiro[chroman-4,4'-imidazolidine]-2-carboxylic acid n-propyl ester (30.0 g, 93.1 mmol) in 800 ml of n-propanol was added methylhydrazine (44.2 g, 0.931 mol). After refluxing the mixture under an argon atmosphere for 18 hours, the reaction mixture was concentrated to half volume and a formed precipitate was removed by filtration. The filtrate was evapolated in vacuo to dryness and to the residue was added 100 ml of water. The resulting crystals were obtained through a filtration and dried in vacuo to give colorless crystals of the desired compound (20.3 g, 70.9%).

Melting point: 276°-278° C.
$[\alpha]_D^{25}$: +137° (c=1.0, methanol).
IR spectrum ($v_{max}^{KBr}$) cm$^{-1}$: 3430, 3060, 1775, 1730, 1660.
NMR spectrum (DMSO-d$_6$) δ ppm:

| | |
|---|---|
| 2.12 | (1H, dd, J=13.7 and 12.7Hz), |
| 2.41 | (1H, dd, J=13.7 and 2.4Hz), |
| 2.47 | (3H, s), |
| 4.97 | (1H, brs), |
| 5.09 | (1H, dd, J=12.2 and 2.4Hz), |
| 6.9-7.2 | (3H, m), |
| 8.39 | (1H, s), |
| 9.85 | (1H, s), |
| 11.02 | (1H, s). |

Mass spectrum (EI/DI) m/z: 308 (M+), 278, 235, 192 (base peak).

EXAMPLE 3

(2S,4S)-6-Fluoro-2',5'-dioxospiro[chroman-4,4'-imidazolidine]-2-(N'-phenyl)carbohydrazide To thionyl chloride (24.9 ml, 3.57 mol) was added (2S,4S)-6-fluoro-2',5'-dioxospiro[chroman-4,4'-imidazolidine]-2-carboxylic acid (20.0 g, 71.4 mmol). After refluxing the mixture under argon atmosphere for 22 hours, the excess thionyl chloride was evaporated in vacuo to dryness to give quantitatively crude crystals of (2S,4S)-6-fluoro-2',5'-dioxospiro[chroman-4,4'-imidazolidine]-2-carbonyl chloride.

To a solution of this acid chloride in 200 ml of N,N-dimethylformamide were added phenylhydrazine (15.6 g, 0.143 mol) and triethylamine (14.4 g, 0.143 mol). After stirring the mixture at 25° C. for 18 hours, 600 ml of water was added to the reaction mixture. The resulting mixture was extracted with ethyl acetate (400 ml×3). The combined ethyl acetate layers were washed with water, dried over anhydrous sodium sulfate, filtered and evaporated in vacuo to dryness. The resulting residue was chromatographed on silica gel, eluted with a mixture of dichloromethane and methanol (20:1) to give colorless crystals (21.3 g, 80.6%). The crystals were recrystallized from 50% aqueous ethanol to give colorless needles of the desired compound (17.4 g, 65.9%).

Melting point: 254°-255° C.
$[\alpha]_D^{25}$: +130° (c=1.0, methanol).
IR spectrum $(v_{max}^{KBr})$ cm$^{-1}$: 3520, 3400, 3060, 1775, 1735, 1670.
NMR spectrum (DMSO-d$_6$) δ ppm:

| |
|---|
| 2.19 (1H, dd, J=13.7 and 12.2Hz), |
| 2.52 (1H, dd, J=13.7 and 2.4Hz), |
| 5.20 (1H, dd, J=12.2 and 2.4Hz), |
| 6.7-6.8 (5H, m), |
| 6.9-7.2 (3H, m), |
| 7.84 (1H, s), |
| 8.39 (1H, s), |
| 10.25 (1H, s), |
| 11.02 (1H, s). |

Mass spectrum (EI/DI) m/z: 370 (M+), 307, 278, 235, 192 (base peak).

EXAMPLE 4

(2S,4S)-6-Fluoro-2',5'-dioxospiro[chroman-4,4'-imidazolidine]-2-(N'-4-chlorophenyl)carbohydrazide This compound was prepared by the same procedure as in the case of Example 3, except that 4-chlorophenylhydrazine (20.4 g, 0.143 mol) was employed for phenylhydrazine to obtain the desired compound (21.7 g, 75.1%).

Melting point: 169°-171° C.
$[\alpha]_D^{25}$: +121° (c=1.0, methanol).
IR spectrum $(v_{max}^{KBr})$ cm$^{-1}$: 3510, 3400, 3060, 1775, 1735, 1670.
NMR spectrum (DMSO-d$_6$) δ ppm:

| |
|---|
| 2.19 (1H, dd, J=13.7 and 12.2Hz), |
| 2.50 (1H, dd, J=13.7 and 2.4Hz), |
| 5.26 (1H, dd, J=12.2 and 2.4Hz), |
| 6.9-7.2 (3H, m), |
| 7.18 (2H, d, J=8.8Hz), |
| 8.00 (1H, s), |
| 8.36 (1H, s), |
| 10.27 (1H, s), |
| 11.01 (1H, s). |

Mass spectrum (EI/DI) m/z: 404 (M+), 192 (base peak).

EXAMPLE 5

(2S,4S)-6-Fluoro-2',5'-dioxospiro[chroman-4,4'-imidazolidine]-2-(N'-4-methoxyphenyl)carbohydrazide This compound was prepared by the same procedure as in the case of Example 3, except that 4-methoxyphenylhydrazine (19.7 g, 0.143 mol) was employed for phenylhydrazine to obtain the desired compound (22.3 g, 78.0%).

Melting point: 154°-157° C.
$[\alpha]_D^{25}$: +127° (c=1.0, methanol).
Ir spectrum $(v_{max}^{KBr})$ cm$^{-1}$: 3400, 3060, 1775, 1730, 1690.
NMR spectrum (DMSO-d$_6$) δ ppm:

| |
|---|
| 2.22 (1H, dd, J=13.7 and 12.2Hz), |
| 2.50 (1H, dd, J=13.7 and 2.4Hz), |
| 5.23 (1H, dd, J=12.2 and 2.4Hz), |
| 6.6-7.2 (7H, m), |
| 7.51 (1H, d, J=3.0Hz), |
| 8.38 (1H, s), |
| 10.22 (1H, d), |
| 11.03 (1H, s). |

Mass spectrum (EI/DI) m/z: 400 (M+), 137 (base peak).

EXAMPLE 6

(2S,4S)-6-Fluoro-2',5'-dioxospiro[chroman-4,4'-imidazolidine]-2-(N'-1-naphthyl)carbohydrazide This compound was prepared by the same procedure as in the case of Example 3, except that 1-naphthylhydrazine hydrochloride (20.4 g, 0.143 mol) was employed for phenylhydrazine to obtain the desired compound (22.7 g, 75.8%).

Melting point: 285°-288° C.
$[\alpha]_D^{25}$: +131° (c=1.0, methanol).
IR spectrum $(v_{max}^{KBr})$ cm$^{-1}$: 3370, 3330, 3060, 1780, 1735, 1680.
NMR spectrum (DMSO-d$_6$) δ ppm:

| |
|---|
| 2.27 (1H, dd, J=13.7 and 12.2Hz), |
| 2.55 (1H, dd, J=13.7 and 2.4Hz), |
| 5.36 (1H, dd, J=12.2 and 2.4Hz), |
| 6.7-8.2 (10H, m), |
| 8.34 (1H, s), |
| 8.38 (1H, s), |
| 10.40 (1H, s), |
| 11.03 (1H, s). |

Mass spectrum (EI/DI) m/z: 420 (M+), 143 (base peak).

EXAMPLE 7

(2S,4S)-6-Fluoro-2',5'-dioxospiro[chroman-4,4'-imidazolidine]-2-hydroxamic acid

To a solution of sodium hydroxide (10.7 g, 0.248 mol) in 400 ml of methanol were added hydroxylamine hydrochloride (13.3 g, 0.186 mol) in 200 ml of methanol and (2S,4S)-6-fluoro-2',5'-dioxospiro[chroman-4,4'-imidazolidine]-2-carboxylic acid n-propyl ester (20.0 g, 62.1 mmol) in 400 ml of methanol. After stirring the mixture at 25° C. for 18 hours, the reaction mixture was evaporated in vacuo to dryness. To the residue was added 200 ml of water and the resulting solution was acidified with concentrated hydrochloric acid and extracted with ethyl acetate (300 ml×4). The combined organic layers were washed with 250 ml of saturated aqueous sodium chloride, dried over anhydrous sodium sulfate, filtered and evaporated in vacuo to give a pale yellow oil (16.8 g, 91.8%). The oil was dissolved in 400 ml of water, treated with active carbon and lyophilized to give a colorless powder of the desired compound (15.0 g, 82.0%).

Melting point: 178° C.

[α]$_D^{25}$: +135° (c=1.0, methanol).

IR spectrum (ν$_{max}^{KBr}$) cm$^{-1}$: 3400, 3060, 1775, 1725, 1680.

NMR spectrum (DMSO-d$_6$) δ ppm:

| |
|---|
| 2.17 (1H, dd, J=13.7 and 12.2Hz), |
| 2.39 (1H, dd, J=13.7 and 2.4Hz), |
| 5.07 (1H, dd, J=12.2 and 2.4Hz), |
| 6.9–7.2 (3H, m), |
| 8.39 (1H, s), |
| 9.11 (1H, s), |
| 11.02 (1H, s), |
| 11.10 (1H, s). |

Mass spectrum (EI/DI) m/z: 295 (M+), 279 (base peak), 235.

REFERENCE EXAMPLE 1

(2S,4S)-6-Fluoro-2',5'-dioxospiro[chroman-4,4'-imidazolidine]-2-carbonyl chloride To thionyl chloride (400 ml, 5.11 mol) was added (2S,4S)-6-fluoro-2',5'-dioxospiro[chroman-4,4'-imidazolidine]-2-carboxylic acid (20.0 g, 67.1 mmol). After refluxing the mixture for 18 hours, the resulting reaction mixture was dried in vacuo to dryness to give the desired compound (20.0 g, 100%).

In the following Examples, the resulting crude product was employed as it was.

EXAMPLE 8

(2S,4S)-N-[2-(4-Cinnamylpiperazin-1-yl)ethyl]-6-fluoro-2',5'-dioxospiro[chroman-4,4'-imidazolidine]-2-carboxamide To a chilled mixture (less than −5° C.) of 4-(2-aminoethyl)-1-cinnamylpiperazine (10.0 g, 40.8 mmol), 1,8-diazabicyclo[5,4,0]-7-undecene (6.20 g, 40.8 mmol) and N,N-dimethylformamide (55.0 ml, 710 mmol) was added over 30 minutes a solution of (2S,4S)-6-fluoro-2',5'-dioxospiro[chroman-4,4'-imidazolidine]-2-carbonyl chloride (Reference Example 1, 11.1 g, 37.1 mmol) in N,N-dimethylformamide (100.1 ml, 1.29 mol). After stirring the mixture for 15 hours at 25° C., the solvent was evaporated. The residue was chromatographed on silica gel, eluted with a mixture of AcOEtAcOEt/MeOH (9:1), and evaporated in vacuo to dryness to give a colorless oil of the desired compound (17.5 g, 92.6%).

Melting point: 133°–135° C.

IR spectrum (ν$_{max}^{KBr}$) cm$^{-1}$: 3412, 2822, 1728, 1665, 1539, 1491.

NMR spectrum (DMSO-d$_6$) δ ppm:

| |
|---|
| 2.28–2.67 (14H, m), |
| 3.16–3.60 (2H, m), |
| 5.07–5.20 (1H, m), |
| 6.27–6.41 (1H, m), |
| 6.55–6.65 (1H, m), |
| 7.00–7.55 (8H, m), |
| 8.15–8.26 (1H, m), |
| 8.41 (1H, s), |
| 11.10 (1H, brs). |

Mass spectrum (EI/DI) m/z: 507 (M+), 217 (base peak).

EXAMPLE 9

(2S,4S)-N-{2-[4-(2-Methoxyphenyl)piperazin-1-yl]ethyl}-6-fluoro-2',5'-dioxospiro[chroman-4,4'-imidazolidine]-2-carboxamide This compound was prepared by the similar procedure as in the case of Example 8, excepting that 4-(2-aminoethyl)-1-(2-methoxyphenyl)pyperazine and (2S,4S)-6-fluoro-2',5'-dioxospiro[chroman-4,4'-imidazolidine]-2-carbonyl chloride (Reference Example 1) were employed.

Yield: 76.9%.

Melting point: 163°–195° C.

IR spectrum (ν$_{max}^{KBr}$) cm$^{-1}$: 3324, 2830, 1728, 1657, 1491, 1242.

NMR spectrum (DMSO-d$_6$) δ ppm:

| |
|---|
| 2.05–2.58 (6H, m), |
| 2.95–2.96 (4H, m), |
| 3.28–3.35 (4H, m), |
| 3.77 (3H, s), |
| 5.13–5.14 (1H, m), |
| 6.85–7.19 (7H, m), |
| 7.15–8.19 (1H, m), |
| 8.35 (1H, s), |
| 10.99 (1H, brs). |

Mass spectrum (EI/DI) m/z: 497 (M+), 205 (base peak).

EXAMPLE 10

(2S,4S)-N-{2-[4-(2-Diphenylmethyl)piperazin-1-yl]ethyl}-6-fluoro-2',5'-dioxospiro[chroman-4,4'-imidazolidine]-2-carboxamide (a) 1-(2-Aminoethyl)-4-diphenylmethylpiperazine A mixture of 1-diphenylmethylpiperazine (30.0 g, 119 mmol), N-(2-bromoethyl)phthalimide (30.3 g, 119 mmol), K$_2$CO$_3$ (16.5 g, 120 mmol) and N,N-dimethylformamide (90.0 ml, 1.16 mol) were stirred for 24 hours at 75° C. After evaporated the solvent in vacuo, the resulting residue was chromatographed on silica gel, eluted with CH$_2$Cl$_2$/MeOH (9/1), and evaporated in vacuo to dryness to give 2-(4-diphenylmethylpiperazin-1-yl)ethylphthalimide (18.1 g, 42.9%).

A mixture of this compound (18.0 g, 42.3 mmol), NH$_2$NH$_2$.H$_2$O (2.50 g, 50.0 mmol) and EtOH (400 ml) was refluxed for 3 hours, cooled and filtered. The resulting filtrate was concentrated in vacuo, chromatographed on silica gel, eluted with AcOEt/NEt$_3$ (1/1)-AcOEt/NEt$_3$/MeOH (5/4/1), and evaporated in vacuo to dryness to give the desired compound (10.6 g, 84.8%).

(b) (2S,4S)-N-{2-[4-(Diphenylmethyl)piperazin-1-yl]ethyl}-6-fluoro-2',5'-dioxospiro[chroman-4,4'-imidazolidine]-2-carboxamide A mixture of 1-(2-aminoethyl)-4-diphenylmethylpiperazine (10.0 g, 33.9 mmol), 1,8-diazabicyclo[5,4,0]-7-undecene (10.9 g, 71.7 mmol) and N,N-dimethylformamide (90.0 ml, 1.16 mol) was chilled to −30° C. To the mixture was added over 30 minutes a solution of (2S, 4S)-6-fluoro-2',5'-dioxospiro[chroman-4,4'-imidazolidine]-2-carbonyl chloride (Reference Example 1, 10.0 g, 33.5 mmol) in N,N-dimethylformamide (90.0 ml, 1.16 mol) and the mixture was stirred for 15 hours at temperature of 15°–25° C. After distilling off the solvent, the reaction mixture was chromatographed on silica gel, eluted with $CH_2Cl_2$/MeOH (9/1) and evaporated in vacuo to dryness to give the desired compound (12.2 g, 65.2%) as colorless amorphous substance.

Melting point: 200°–205° C.

IR spectrum ($v_{max}^{KBr}$) cm$^{-1}$: 3400, 2810, 1780, 1730, 1665, 1490.

NMR spectrum (DMSO-d$_6$) δ ppm:

| |
|---|
| 2.07–3.73 (14H, m), |
| 4.32 (1H, s), |
| 5.11–5.16 (1H, m), |
| 6.89–7.50 (13H, m), |
| 8.24–8.29 (1H, m), |
| 8.47 (1H, s), |
| 11.12 (1H, brs). |

Mass spectrum (EI/DI) m/z: 557 (M+), 167 (base peak).

EXAMPLE 11

(2S,4S)-N-[2-(4-Benzylpiperidin-1-yl)ethyl]-6-fluoro-2'5'-dioxospiro[chroman-4,4'-imidazolidine]-2-carboxamide A mixture of N-(2-aminoethyl)-4-benzylpiperidine (13.0 g, 59.6 mmol), 1,8-diazabicyclo[5,4,0]-7-undecene (10.9 g, 71.7 mmol) and N,N-dimethylformamide (90.0 ml, 1.16 mol) was chilled to −30° C. To the mixture was added over 30 minutes a solution of (2S, 4S)-6-fluoro-2',5'-dioxospiro[chroman-4,4'-imidazolidine]-2-carbonyl chloride (Reference Example, 18.0 g, 60.3 mmol) in N,N-dimethylformamide (90.0 ml, 1.16 mol) and the mixture was stirred for 15 hours at temperature of 15°–25° C. After distilling off the solvent, the reaction mixture was chromatographed on silica gel, eluted with $CH_2Cl_2$/MeOH (9/1) and evaporated in vacuo to dryness to give the desired compound (14.3 g, 50.0%) as colorless amorphous substance.

Melting point: 231°–232° C.

IR spectrum ($v_{max}^{KBr}$) cm$^{-1}$: 3230, 2925, 1785, 1725, 1655, 1490.

NMR spectrum (DMSO-d$_6$) δ ppm:

| |
|---|
| 1.15–2.70 (13H, m), |
| 2.85–3.03 (2H, m), |
| 3.29–3.44 (2H, m), |
| 5.18–5.21 (1H, m), |
| 7.09–7.43 (8H, m), |
| 8.15–8.40 (1H, s), |
| 8.52 (1H, s), |
| 11.00 (1H, brs). |

Mass spectrum (EI/DI) m/z: 480 (M+), 188 (base peak).

EXAMPLE 12

(2S,4S)-N-{2-[4-(3,4,5-Trimethoxycinnamoyl)piperazin-1-yl]ethyl}-6-fluoro-2',5'-dioxospiro[chroman-4,4'-imidazolidine]-2-carboxamide 3,4,5-Trimethoxycinnamic acid was chlorinated with $SOCl_2$ to convert into 3,4,5-trimethoxycinnamoyl chloride which was reacted with piperazine, in a 6 fold amount to synthesize 1-(3,4,5-trimethoxycinnamoyl)-piperazine, with a yield of 42.6%. Then, this compound was reacted in a conventional manner with N-(2-bromoethyl)phthalimide to synthesize N-{[2-(3,4,5-trimethoxycinnnamoypiperazin)-1-yl]ethyl}phthalimide with yield of 55.0%. This compound and $NH_2NH_2.H_2O$ in equi-amount were refluxed in a mixed solvent of MeOH/CHCl$_3$ for 6 hours to synthesize 4-(2-aminoethyl)-1-(3,4,5-trimethoxycinnamoyl)piperazine with yield of 66.9%.

The procedure similar to that described in Example 8 was carried out with the use of the compound of 4-(2-aminoethyl)-1-(3,4,5-trimethoxycinnamoyl)piperazine and (2S,4S)-6-fluoro-2',5'-dioxospiro[chroman-4,4'-imidazolidine]-2-carbonyl chloride (Reference Example 1) to give the desired compound with yield of 72.0%.

Melting point: <183° C.

IR spectrum ($v_{max}^{KBr}$) cm$^{-1}$: 3400, 2940, 1780, 1730, 1645, 1490.

NMR spectrum (DMSO-d$_6$) δ ppm:

| |
|---|
| 2.14–2.65 (8H, m), |
| 3.33–3.92 (6H, m), |
| 3.85 (3H, s), |
| 3.87 (6H, s), |
| 5.24–5.28 (1H, m), |
| 6.70–7.58 (8H, m). |

Mass spectrum (EI/DI) m/z: 221 (base peak).

EXAMPLE 13

(2S, 4S)-N-(2-Nitroxyethyl)-6-fluoro-2',5'-dioxospiro[chroman-4,4'-imidazolidine]-2-carboxamide The procedure similar to that as described in Example 8 was carried out with use of 2-nitroxyethylamine and (2S,4S)-6-fluoro-2',5'-dioxospiro[chroman-4,4'-imidazolidine]-2-carbonyl chloride (Reference Example 1) to give the desired compound.

Yield: 82.3%.

Melting point: 266°–271° C.

IR spectrum ($v_{max}^{KBr}$) cm$^{-1}$: 3420, 1780, 1730, 1645, 1490, 1280.

NMR spectrum (DMSO-d$_6$) δ ppm:

| |
|---|
| 1.99–2.49 (2H, m), |
| 3.44–3.53 (2H, m), |
| 4.59 (2H, t, J=5Hz), |
| 5.07–5.13 (1H, m), |
| 6.97–7.20 (3H, m), |
| 8.40 (1H, s), |
| 8.54–8.59 (1H, m), |
| 11.03 (1H, s). |

Mass spectrum (EI/DI) m/z: 305 (M+−63), 114 (base peak).

EXAMPLE 14

(2S,4S)-N-{2-[(Imidazol-1-yl)ethyl]}-6-fluoro-2',5'-dioxospiro[chroman-4,4'-imidazolidine]-2-carboxamide The procedure similar to that as described in Example 8 was carried out with use of 1-(2-aminoethyl)imidazole and (2S,4S)-6-fluoro-2',5'-dioxospiro[chroman-4,4'-imidazolidine]-2-carbonyl chloride (Reference Example 1) to give the desired compound.

Yield: 72.6%.

Melting point: 151°–153° C.

IR spectrum ($v_{max}^{KBr}$) cm$^{-1}$: 3432, 1722, 1491, 1262, 1121.

NMR spectrum (DMSO-d$_6$) δ ppm:

| |
|---|
| 2.10–2.63 (2H, m), |

| | |
|---|---|
| 3.50–3.70 | (2H, m), |
| 4.20–4.24 | (2H, m), |
| 5.17–5.22 | (1H, m), |
| 6.99 | (1H, s), |
| 7.07–7.30 | (4H, m), |
| 7.68 | (1H, s), |
| 8.49–8.52 | (2H, m), |
| 11.11 | (1H, brs). |

Mass spectrum (EI/DI) m/z: 373 (M+), 138 (base peak).

REFERENCE EXAMPLE 2

(2S,4S)-1'-(3-Chloropropyl)-6-fluoro-2',5'-dioxospiro[chroman-4,4'-imidazolidine]-2-carboxamide To a solution of (2S,4S)-6-fluoro-4',5'-dioxospiro[chroman-4,4'-imidazolidine]-2-carboxamide (27.9 g, 100 mmol) in N,N-dimethylformamide (150 ml, 1.94 mmol) was added 1-bromo-3-chloropropane (31.5 g, 200 mmol). After adding 60% NaH (4.00 g, 100 mmol) over 30 minutes at 15°–20° C., the mixture was stirred for 15 hours at 25°–30° C. The reaction mixture was poured into iced water (500 ml), extracted with AcOEt (1000 ml×3), dried over MgSO₄. The solvent was distilled off, the residue was chromatographed on silica gel, eluted with $CH_2Cl_2$-$CH_2Cl_2$/MeOH (5/1) to give the desired compound (28.8 g, 81.0%) as colorless prism crystals.

Melting point: 174°–176° C.
Mass spectrum (EI/DI) m/z: 355 (M+, base peak).

EXAMPLE 15

(2S,4S)-1'-[3-(4-Hydroxypiperidin-1-yl)propyl]-6-fluoro-2',5'-dioxospiro[chroman-4,4'-imidazolidine]-2-carboxamide A mixture of (2S,4S)-1'-(3-chloropropyl)-6-fluoro-2',5'-dioxospiro[chroman-4,4'-imidazolidine]-2-carboxamide (Reference Example 2, 15.0 g, 42.2 mmol), 4-hydroxypiperidine (8.52 g, 84.4 mmol), K₂CO₃ (7.00 g, 50.7 mmol) and N,N-dimethylformamide (100 ml, 1.29 mol) was stirred for 5 hours at 80° C. After distilling off the solvent, the residue was chromatographed on silica gel, eluted with $CH_2Cl_2$/MeOH/NEt₂ (5/1/1), and recrystallized from AcOEt/MeOH to give prism crystals of the desired compound (16.2 g, 91.5%).

Melting point: 208°–209° C.
IR spectrum ($\nu^{KBr}_{max}$) cm⁻¹: 3500, 3380, 1780, 1725, 1495, 1120.
NMR spectrum (DMSO-d₆) δ ppm:

| | |
|---|---|
| 1.28–2.67 | (15H, m), |
| 3.16–3.44 | (2H, m), |
| 4.48 | (1H, m), |
| 5.07–5.02 | (1H, m), |
| 7.20–6.89 | (3H, m), |
| 7.52 | (1H, s), |
| 7.75 | (1H, s), |
| 8.67 | (1H, s). |

Mass spectrum (EI/DI) m/z: 420 (M+), 114 (base peak).

REFERENCE EXAMPLE 3

(2S,4S)-N-Ethyl-1'-(3-chloropropyl)-6-fluoro-2',5'-dioxospiro[chroman-4,4'-imidazolidine]-2-carboxamide To a solution of (2S,4S)-N-ethyl-6-fluoro-2',5'-dioxospiro[chroman-4,4'-imidazolidine]-2-carboxamide (21.0 g, 68.4 mmol) in N,N-dimethylformamide (100 ml, 1.29 mmol) was added 1-bromo-3-chloropropane (21.5 g, 137 mmol). After adding 60% NaH (2.75 g, 68.8 mmol) over 30 minutes at 15°–20° C., the mixture was stirred for 15 hours at 15°–25° C. The reaction mixture was poured into iced water (500 ml), extracted with AcOEt (1000 ml×3), dried over MgSO₄. The solvent was distilled off, the residue was chromatographed on silica gel, eluted with $CH_2Cl_2$-$CH_2Cl_2$/MeOH (9/1), and recrystallized from AcOEt to give the desired compound (19.3 g, 73.8%) as colorless prism crystals.

Melting point: 95°–97° C.
Mass spectrum (EI/DI) m/z: 383 (M+, base peak).

EXAMPLE 16

(2S,4S)-N-Ethyl-1'-[3-(4-hydroxypiperidin-1-yl)propyl]-6-fluoro-2',5'-dioxospiro[chroman-4,4'-imidaxolidine]-2-carboxamide A mixture of (2S,4S)-N-ethyl-1'-(3-chloropropyl)-6-fluoro-2',5'-dioxospiro[chroman-4,4'-imidazolidine]-2-carboxamide (Reference Example 3, 18.0 g, 46.9 mmol), 4-hydroxypiperidine (9.47 g, 93.8 mmol), K₂CO₃ (7.77 g, 56.3 mmol) and N,N-dimethylformamide (90.0 ml, 1.17 mol) was stirred for 5.5 hours at 80°–85° C. After distilling off the solvent, the residue was chromatographed on silica gel, eluted with $CH_2Cl_2$/MeOH (9/1), and evaporated in vacuo to dryness to give amorphous crystals of the desired compound (17.8 g, 84.8%).

Melting point: 98°–100° C.
IR spectrum ($\nu_{max}^{KBr}$) cm⁻¹: 3430, 1775, 1720, 1715, 1495.
NMR spectrum (DMSO-d₆) δ ppm:

| | |
|---|---|
| 1.13 | (3H, t, J=7Hz), |
| 1.36–2.28 | (17H, m), |
| 3.19–3.55 | (2H, m), |
| 4.58 | (1H, m), |
| 5.12–5.18 | (1H, m), |
| 7.28–6.97 | (3H, m), |
| 8.41 | (1H, m), |
| 8.75 | (1H, s). |

Mass spectrum (EI/DI) m/z: 448 (M+), 114 (base peak).

REFERENCE EXAMPLE 4

(2S,4S)-N-Butyl-1'-(3-chloropropyl)-6-fluoro-2',5'-dioxospiro[chroman-4,4'-imidazolidine]-2-carboxamide To a solution of (2S,4S)-N-butyl-6-fluoro-2',5'-dioxospiro[chroman-4,4'-imidazolidine]-2-carboxamide (25.0 g, 74.6 mmol) in N,N-dimethylformamide (125 ml, 1.62 mmol) was added 1-bromo-3-chloropropane (23.5 g, 149 mmol). After adding 60% NaH (3.00 g, 75.0 mmol) over 30 minutes at 15°–22° C., the mixture was stirred for 5 hours at 25°–28° C. The reaction mixture was poured into iced water (500 ml), extracted with AcOEt (1000 ml×3), dried over MgSO₄. The solvent was distilled off, the residue was chromatographed on silica gel, eluted with $CH_2Cl_2$-$CH_2Cl_2$/MeOH (9/1), and recrystallized from AcOEt to give the desired compound (24.7 g, 80.5%) as colorless prism crystals.

Melting point: 148°–150° C.
Mass spectrum (EI/DI) m/z: 341 (M+, base peak).

EXAMPLE 17

(2S,4S)-N-Butyl-1'-[3-(4-hydroxypiperidin-1-yl)propyl]-6-fluoro-2',5'-dioxospiro[chroman-4,4'-imidazolidine]-2-carboxamide A mixture of (2S,4S)-N-butyl-1'-(3-chloropropyl)-6-fluoro-2',5'-dioxospiro[chroman-4,4'-imidazolidine]-2-carboxamide (Reference Example 4, 17.0 g, 41.4 mmol), 4-hydroxypiperidine (8.36 g, 82.8 mmol), $K_2CO_3$ (7.43 g, 53.8 mmol) and N,N-dimethylformamide (68.0 ml, 880 mmol) was stirred for 5 hours at 80° C. After distilling off the solvent, the residue was chromatographed on silica gel, eluted with $CH_2Cl_2$/MeOH (9/1), and evaporated in vacuo to dryness to give amorphous crystals of the desired compound (18.8 g, 95.4%).

Melting point: 86°–88° C.

IR spectrum $(\nu_{max}^{KBr})$ cm$^{-1}$: 3400, 1775, 1710, 1660, 1490.

NMR spectrum (DMSO-d$_6$) δ ppm:

| |
|---|
| 0.95 (3H, t, J=7Hz), |
| 1.22–2.80 (19H, m), |
| 3.17–3.25 (2H, m), |
| 3.46–3.54 (2H, m), |
| 4.58–4.65 (1H, m), |
| 5.14–5.19 (1H, m), |
| 6.98–7.28 (3H, m), |
| 8.31–8.41 (1H, m), |
| 8.75 (1H, s). |

Mass spectrum (EI/DI) m/z: 476 (M+), 114 (base peak).

PRESCRIPTION EXAMPLE 1

Tablets were prepared in a conventional manner with use of following components.

| | |
|---|---|
| Hydantoin compound (Example 3) | 50 (mg) |
| Sodium citrate | 25 |
| Arginine | 10 |
| Polyvinylpyrrolidone | 10 |
| Magnesium stearate | 5 |
| (Total) | 100 mg/tablet |

PRESCRIPTION EXAMPLE 2

Tablets were prepared in a prescription similar to that as in Prescription Example 1, excepting that a product of Example 11 was selected as the effective ingredient, instead of that of Example 3.

PRESCRIPTION EXAMPLE 3

Tablets were prepared in a prescription similar to that as in Prescription Example 1, excepting that a product of Example 17 was selected as the effective ingredient, instead of that of Example 3.

Pharmacological Test Example 1

Acute toxicity

Each of the hydantoin compounds according to the invention was orally given to female mice to check the acute toxicity. A value of LD$_{50}$ was calculated in accordance with the Litchfield-Wilcoxon method to find it is more than 5000 mg/kg. This means that the compounds of the invention has quite low toxicity.

Pharmacological Test Example 2

Inhibition to aldose reductase

An ability for reducing or inhibiting activity of aldose reductase was checked, in accordance with the method of Kador et al as described in "Biophys. Chem." Vol. 8, page 81 (1978) and by selecting the hydantoin derivatives according to the invention, as—Test Compounds—and d-isomer of 6-fluorospiro[chroman-4,4'-imidazolidine]-2',5'-dione [—Sorbinil—which is one of exemplary compounds among those described in Jap. Pat. Sho 53-53653(A), discussed supra], as—Control Compound—.

Results are shown in following Table 1. As apparently seen from the Table, each of the derivatives according to the invention shows a relatively high inhibition activity to the aldose reductase.

TABLE 1

| Compounds | IC$_{50}$ (M) (*) |
|---|---|
| Test Compounds Example | |
| 1 | 3.8 × 10$^{-8}$ |
| 2 | 3.0 × 10$^{-7}$ |
| 3 | 2.2 × 10$^{-8}$ |
| 4 | 2.6 × 10$^{-8}$ |
| 5 | 4.4 × 10$^{-8}$ |
| 6 | 1.3 × 10$^{-8}$ |
| 7 | 3.7 × 10$^{-8}$ |
| 8 | 2.2 × 10$^{-7}$ |
| 9 | 2.4 × 10$^{-7}$ |
| 10 | 1.5 × 10$^{-7}$ |
| 11 | 1.9 × 10$^{-6}$ |
| 12 | 1.5 × 10$^{-7}$ |
| 13 | 1.9 × 10$^{-7}$ |
| 14 | 6.5 × 10$^{-7}$ |
| Control Compound | |
| Sorbinil | 2.0 × 10$^{-7}$ |

In the Table,
(*) 50% Inhibitory Concentration

PHARMACOLOGICAL TEST EXAMPLE 3

Inhibition of platelet agglutination

A blood was taken from a descending aorta of the rat anesthetized with ethyl ether. To the blood, 3.8% aqueous sodium citrate was added by a volume of 1/3 and the resulting solution was centrifuged (1500 rpm) at 4° C. for 10 minutes to obtain a supernatant which was designated as "PRP (platelet rich plasma)". The remaining residue was centrifuged (3000 rpm) at 4° C. for 10 minutes to obtain a supernatant which was designated as "PPP (platelet poor plasma)". A stirrer bar and PRP (267 μl) were inserted in a cell and PPP (more than 300 μl) was charged in another cell. A transmissivity to PRP and PPP was measured and set as "0%" for the former case and as "100%" for the latter case.

After a preincubation for 1 minute, a compound to be tested was added by 3 μl and then an agglutination causing substance (collagen or ADP) was added by 30 μl at a time lapsed of 1 minute from the addition of testing compound. For a control group, 3 μl of dimethylsulfoxide was added, instead of the testing compound. A maximum value in transmissivity change after the addition of agglutination causing substance was determined and made as a platelet agglutination rate (%). Further, the inhibition was checked by setting as 100% for a level on each control to calculate 50% inhibition concentration (IC$_{50}$).

Results are shown in following Table 2. As apparently seen therefrom, the compounds according to the invention show an excellent inhibition to the platelet agglutination.

TABLE 2

| Compounds | $IC_{50}$ | |
|---|---|---|
| | Collagen | ADP |
| Control | | |
| Indomethacin | $6.8 \times 10^{-5}$ | N.D. |
| Aspirin | $2.1 \times 10^{-4}$ | N.D. |
| Test compound Example | | |
| 3 | $1.4 \times 10^{-4}$ | N.D. |
| 4 | $1.8 \times 10^{-4}$ | N.D. |
| 5 | $2.6 \times 10^{-5}$ | N.D. |
| 6 | $2.3 \times 10^{-4}$ | N.D. |
| 8 | $2.5 \times 10^{-4}$ | N.D. |
| 9 | $6.6 \times 10^{-4}$ | N.D. |
| 10 | $4.1 \times 10^{-4}$ | $7.0 \times 10^{-4}$ |
| 11 | $8.3 \times 10^{-5}$ | $3.7 \times 10^{-4}$ |
| 13 | $2.4 \times 10^{-4}$ | N.D. |

In the Table,
N.D. : not detected.

PHARMACOLOGICAL TEST EXAMPLE 4

Action to the aorta of guinea pig

Hartley guinea pigs (body weight of 300–500 g) were rendered unconscious fainted by knocking their head and fixed upwardly. A thoracic aorta was taken out to prepare spiral samples, each having size of about 2×25 mm. The sample was suspended in a Magnus tube under a load of about 1 g and upper end of the sample was connected through a silk thread to a FD pick-up to record a change in isometric tension.

In the Magnus tube, 10 ml of Krebs-Henseleit solution with following composition kept at 37° C. was accommodated and 95% $O_2$/5% $CO_2$ gas was lead therein.

Composition of Krebs-Henseleit solution:

| | | |
|---|---|---|
| NaCl | 118 | (mM) |
| KCl | 4.7 | |
| $CaCl_2$ | 2.55 | |
| $MgSO_4$ | 1.18 | |
| $KH_2PO_4$ | 1.18 | |
| $NaHCO_3$ | 24.88 | |
| Glucose | 11.1 | |

Prior to the experiment, the sample in the Magnus tube was left to stand, as it was, for 60 to 90 minutes and in such period of time, the Krebs-Henseleit solution was exchanged to fresh one at an interval of 20 to 30 minutes.

After attained in such a state that a recorder shows a stable tensile force, KCl was added in a amount of $2.5 \times 10^{-2}$ M in final concentration or norepinephrine was added in a amount of $10^{-6}$ g/ml in final concentration. When the contraction of the sample became constant, the compound to be tested was gradually added in a amount starting at a concentration of $10^{-8}$, to $10^6$ M to observe the contraction of the sample. Finally, papaverine was added therein, so as to make its final concentration of $2 \times 10^{-5}$ g/ml, to check and record also the relaxing reaction or atony caused by the papaverine.

By setting the relaxing rate at stable time after the addition of KCl or norepinephrine as 100%, a relative value in the reaction for each concentration was calculated and 50% relaxing ($IC_{50}$) was calculated for data analysis.

Results are shown in following Table 3.

TABLE 3

| Compounds | $IC_{50}$ (M) | |
|---|---|---|
| | KCl contraction | N.E. contraction |
| Test Example | | |
| 1 | $9.5 \times 10^{-5}$ | $2.0 \times 10^{-6}$ |
| 2 | $>10^{-3}$ | $>10^{-3}$ |
| 3 | $3.0 \times 10^{-5}$ | $8.0 \times 10^{-7}$ |
| 4 | $>10^{-3}$ | $>10^{-3}$ |
| 5 | $5.0 \times 10^{-6}$ | $3.0 \times 10^{-5}$ |
| 7 | $>10^{-3}$ | $>10^{-3}$ |
| 8 | $>10^{-3}$ | $>10^{-3}$ |
| 9 | $>10^{-3}$ | $>10^{-3}$ |
| 10 | $1.8 \times 10^{-6}$ | $1.0 \times 10^{-4}$ |
| 11 | $1.9 \times 10^{-6}$ | $1.0 \times 10^{-7}$ |
| 12 | $1.6 \times 10^{-4}$ | $3.0 \times 10^{-5}$ |
| 13 | $6.0 \times 10^{-5}$ | $2.0 \times 10^{-5}$ |
| 14 | $>10^{-3}$ | $>10^{-3}$ |
| 15 | $8.0 \times 10^{-6}$ | $2.0 \times 10^{-6}$ |
| 16 | $5.9 \times 10^{-5}$ | $5.0 \times 10^{-6}$ |
| 17 | $1.0 \times 10^{-6}$ | $3.0 \times 10^{-5}$ |
| Control | | |
| Cinepazide | $2.0 \times 10^{-3}$ | $1.0 \times 10^{-3}$ |
| Cinnarizine | $2.0 \times 10^{-4}$ | $1.0 \times 10^{-4}$ |

In the Table,
N.E. : norepinephrine.

PHARMACOLOGICAL TEST EXAMPLE 5

Action to heart of guinea pig

Hartley guinea pigs (body weight of 300–400 g) were rendered unconscious by knocking their head and fixed upwardly to exenterate their heart. The heart was inserted in a beaker accommodating a Krebs-Henseleit solution (see Pharmacological Test Example 4) under 95% $O_2$/5% $CO_2$ gas atmosphere, to wash out blood adhering thereto and then transferred the heart to a glass vessel for preparing a sample. The vessel was previously filled with the Krebs-Henseleit solution and the said mixed gas was continuously fed therein.

Samples were prepared by separating from a ventricular muscle a right and left atrium, along an auricloventricular furrow or groove from the center-line of the right and left auricles.

(a) As to the right atrium sample

The right atrium sample was suspended in a Magnus tube fed 95% $O_2$/5% $CO_2$ gas and accommodating 10 ml of the Krebs-Henseleit solution kept at 32°±1° C., so that tensile force of the sample became 0.2–0.3 g. A contraction of the sample, due to a compound to be tested, was recorded through an FD pick-up. Concurrently, pulsations were input to a measuring unit to count and record number of the pulsations.

(b) As to left atrium sample

The left atrium sample was suspended with a cellfin through both auricles to a Magnus tube fed 95% $O_2$/5% $CO_2$ gas and accommodating 10 ml of the Krebs-Henseleit solution kept at 32°±1° C., so that the braking tensile force of the sample became about 0.25 g. The atrium was driven by contacting it with a platinum bipolar electrode attached to the cellfin and by stimulating the same with a rectangular pulse (1 Hz, 1 msec, 10 V). A movement of the sample was recorded by connecting the sample to a recorder through a silk thread and a FD pick-up.

In following Table 4, the affects of the compounds are given according to the invention and control compounds to the right atrium (countering the pulsations) and to the left atrium (measuring contraction power of heart).

TABLE 4

| Compounds | Pulsation | | Contraction | |
|---|---|---|---|---|
| | $10^{-5}$(M) | $10^{-4}$(M) | $10^{-5}$(M) | $10^{-4}$(M) |
| Test Example | | | | |
| 3 | − | − | − | + |
| 4 | − | + | − | + |
| 5 | − | − | − | + |
| 6 | − | + | − | + |
| 8 | − | + | − | + |
| 9 | − | − | − | + |
| 10 | + | ++ | − | − |
| 11 | + | ++ | − | + |
| 12 | − | − | − | ++ |
| 15 | − | − | − | − |
| 16 | − | + | − | − |
| 17 | − | + | + | ++ |
| Control | | | | |
| A | ++ | ++ | ++ | ++ |
| B | ++ | ++ | − | + |

In the Table,
A : Propranolol,
B : Ifenprodil,
− : No recognizable influence,
+ : Inhibition of 10-20%, and
++ : Inhibition of more than 20%.

PHARMACOLOGICAL TEST EXAMPLE 6

Influences of compounds according to the invention upon the blood pressure and cardiac pulsation were checked with use of Hartley guinea pigs, as experimental animal.

Results are shown in following Table 5.

TABLE 5

| Compound | Dose | Change in blood pressure | Change in cardiac pulsation |
|---|---|---|---|
| Control | — | −1.1 ± 1.5 | −0.1 ± 0.5 |
| Test Example | | | |
| 15 | 3 | −2.6 ± 1.8 | 0.0 ± 0.0 |
| | 10 | −12.2 ± 5.6 | −5.4 ± 2.9 |
| 16 | 3 | −4.0 ± 4.0 | −1.2 ± 1.2 |
| | 10 | −21.3 ± 2.4 (*) | −4.7 ± 4.6 |
| 17 | 3 | −3.0 ± 3.0 | −1.1 ± 1.1 |
| | 10 | −43.8 ± 4.9 (*) | −48.9 ± 2.2 (*) |

In the Table,
Dose : mg/kg, i.v.,
Change in blood pressure : %,
Change in cardiac pulsation : %
Control : Physiological saline, and
(*) : There is a significance difference (p < 0.001).

What is claimed is:

1. A hydantoin derivative selected from the group consisting of
a) (2S,4S)-6-fluoro-2',5'-dioxospiro[chroman-4,4'-imidazolidine]-2-carbohydrazide,
b) (2S,4S)-6-fluoro-2',5'-dioxospiro[chroman-4,4'-imidazolidine]-2-(N'-methyl)carbohydrazide,
c) (2S,4S)-6-fluoro-2',5'-dioxospiro[chroman-4,4'-imidazolidine]-2-(N'-phenyl)carbohydrazide,
d) (2S,4S)-6-fluoro-2',5'-dioxospiro[chroman-4,4'-imidazolidine]-2-(N'-4-chlorophenyl)carbohydrazide,
e) (2S,4S)-6-fluoro-2',5'-dioxospiro[chroman-4,4'-imidazolidine]-2-(N'-4-methoxyphenyl)carbohydrazide,
f) (2S,4S)-6-fluoro-2',5'-dioxospiro[chroman-4,4'-imidazolidine]-2-(N'-1-naphthyl)carbohydrazide,
g) (2S,4S)-6-fluoro-2',5'-dioxospiro[chroman-4,4'-imidazolidine]-2-hydroxamic acid,
h) (2S,4S)-N-[2-(4-cinnamylpiperazin-1-yl)ethyl]-6-fluoro-2',5'-dioxospiro[chroman-4,4'-imidazolidine]-2-carboxamide,
i) (2S,4S)-N-{2-[4-(2-methoxyphenyl)piperazin-1-yl]ethyl}-6-fluoro-2',5'-dioxospiro[chroman-4,4'-imidazolidine]-2-carboxamide,
j) (2S,4S)-N-{2-[4-(diphenylmethyl)piperazin-1-yl]ethyl}-6-fluoro-2',5'-dioxospiro[chroman-4,4'-imidazolidine]-2-carboxamide,
k) (2S,4S)-N-[2-(4-benzylpiperadin-1-yl)ethyl]-6-fluoro-2',5-dioxospiro[chroman-4,4'-imidazolidine]-2-carboxamide,
l) (2S,4S)-N-{2-[4-(3,4,5-trimethoxycinnamoylpiperozin-1-yl]ethyl}-6-fluoro-2',5'-dioxospiro[chroman-4,4'-imidazolidine]-2-carboxamide,
m) (2S,4S)-N-(2-nitroxyethyl)-6-fluoro-2',5'-dioxospiro[chroman-4,4'-imidazolidine]-2-carboxamide,
n) (2S,4S)-N-{2-[(imidazol-1-yl)ethyl]}-6-fluoro-2',5'-dioxospiro[chroman-4,4'-imidazolidine]-2-carboxamide,
o) (2S,4S)-1'-[3-(4-hydroxypiperidin-1-yl)propyl]-6-fluoro-2',5'-dioxospiro[chroman-4,4'-imidazolidine]-2-carboxamide,
p) (2S,4S)-N-ethyl-1'-[3-(4-hydroxypiperidin-1-yl)propyl]-6-fluoro-2',5'-dioxospiro[chroman-4,4'-imidazolidine]-2-carboxamide, and
q) (2S,4S)-N-butyl-1'-[3-(4-hydroxypiperidin-1-yl)propyl]-6-fluoro-2',5'-dioxospiro[chroman-4,4'-imidazolidine]-2-carboxamide.

2. A composition for treating circulatory diseases, complications of diabetes, or both, which comprises an effective amount of a hydantoin derivative selected from the group consisting of
a) (2S,4S)-6-fluoro-2',5'-dioxospiro[chroman-4,4'-imidazolidine]-2-carbohydrazide,
b) (2S,4S)-6-fluoro-2',5'-dioxospiro[chroman-4,4'-imidazolidine]-2-(N'-methyl)carbohydrazide,
c) (2S,4S)-6-fluoro-2',5'-dioxospiro[chroman-4,4'-imidazolidine]-2-(N'-phenyl)carbohydrazide,
d) (2S,4S)-6-fluoro-2',5'-dioxospiro[chroman-4,4'-imidazolidine]-2-(N'-4-chlorophenyl)carbohydrazide,
e) (2S,4S)-6-fluoro-2',5'-dioxospiro[chroman-4,4'-imidazolidine]-2-(N'-4-methoxyphenyl)carbohydrazide,
f) (2S,4S)-6-fluoro-2',5'-dioxospiro[chroman-4,4'-imidazolidine]-2-(N'-1-naphthyl)carbohydrazide,
g) (2S,4S)-6-fluoro-2',5'-dioxospiro[chroman-4,4'-imidazolidine]-2-hydroxamic acid,
h) (2S,4S)-N-[2-(4-cinnamylpiperazin-1-yl)ethyl]-6-fluoro-2',5'-dioxospiro[chroman-4,4'-imidazolidine]-2-carboxamide,
i) (2S,4S)-N-{2-[4-(2-methoxyphenyl)piperazin-1-yl]ethyl}-6-fluoro-2',5'-dioxospiro[chroman-4,4'-imidazolidine]-2-carboxamide,
j) (2S,4S)-N-{2-[4-(2-diphenylmethyl)piperazin-1-yl]ethyl}-6-fluoro-2',5'-dioxospiro[chroman-4,4'-imidazolidine]-2-carboxamide,
k) (2S,4S)-N-[2-(4-benzylpiperadin-1-yl)ethyl]-6-fluoro-2',5'-dioxospiro[chroman-4,4'-imidazolidine]-2-carboxamide,
l) (2S,4S)-N-{2-[4-(3,4,5-trimethoxycinnamoyl-piperazin-1-yl]ethyl}-6-fluoro-2',5'-dioxospiro[chroman-4,4'-imidazolidine]-2-carboxamide, m)  (2S,4S)-N-(2-nitroxyethyl)-6-fluoro-2',5'-dioxospiro[chroman-4,4'-imidazolidine]-2-carboxamide, n)  (2S,4S)-N-{2-[(imidazol-1-yl)ethyl]}-6-fluoro-2',5'-dioxospiro[chroman-4,4'-imidazolidine]-2-carboxamide, o)  (2S,4S)-1'-[3-(4-hydroxypiperidin-1-yl)propyl]-6-fluoro-2',5'-dioxospiro[chroman-4,4'-imidazolidine]-2-carboxamide, p)  (2S,4S)-N-ethyl-1'-[3-(4-hydroxypiperidin-1-yl)propyl]-6-fluoro-2',5'-dioxospiro[chroman-4,4'-imidazolidine]-2-carboxamide, and q)  (2S,4S)-N-butyl-1'-[3-(4-hydroxypiperidin-1-yl)propyl]-6-fluoro-2',5'-dioxospiro[chroman-4,4'-imidazolidine]-2-carboxamide.

* * * * *